United States Patent [19]

Demmin et al.

[11] Patent Number: 5,705,779
[45] Date of Patent: Jan. 6, 1998

[54] PREPARATION OF 1,1,1,3,3-PENTACHLOROPROPANE BY PHOTOCHLORINATION OF 1,1,1,3-TETRACHLOROPROPANE

[75] Inventors: Timothy Rech Demmin, Grand Island, N.Y.; Valeriy Georglevitch Barabanov, St. Petersburg, Russian Federation; Svetlana Ivanovna Ozol, St. Petersburg, Russian Federation; Victor Grigorievitch Temchenko, St. Petersburg, Russian Federation

[73] Assignee: AlliedSignal Inc., Morristown, N.J.

[21] Appl. No.: 694,138

[22] Filed: Aug. 8, 1996

[51] Int. Cl.[6] .................. C07F 1/00; C07F 3/00; C07C 17/00; C07C 19/00
[52] U.S. Cl. .................. 204/157.6; 204/157.63; 204/157.94; 570/101
[58] Field of Search .................. 204/157.6, 157.63, 204/157.94; 570/101

[56] References Cited

FOREIGN PATENT DOCUMENTS

| 601912 | 5/1979 | U.S.S.R. |
| 1055410 | 1/1967 | United Kingdom |

OTHER PUBLICATIONS

Rotshtein et al., "Distribution of Isomers During the Chlorination of Chloropropanes", Zh. Org. Khim., Vol. 7, No. 1, pp. 26–27 (abstract only), ?/1971, month unavailable.

Primary Examiner—Kathryn L. Gorgos
Assistant Examiner—Edna Wong
Attorney, Agent, or Firm—Jay P. Friedenson

[57] ABSTRACT

A process for the preparation of 1,1,1,3,3-pentachloropropane (HCC-240fa). HCC-240fa is prepared by the photochlorination of 1,1,1,3-tetrachloropropane (HCC-250). HCC-240fa is an important intermediate in the preparation of 1,1,1,3,3-pentafluoropropane (HFC-245fa) an HFC blowing agent which is not destructive to the ozone layer.

20 Claims, No Drawings

PREPARATION OF 1,1,1,3,3-PENTACHLOROPROPANE BY PHOTOCHLORINATION OF 1,1,1,3-TETRACHLOROPROPANE

BACKGROUND OF THE INVENTION

1. Field of the Invention

The present invention relates to a process for the preparation of 1,1,1,3,3-pentachloropropane (HCC-240fa). More particularly, the invention pertains to an improved process for the preparation of HCC-240fa by the photochlorination of 1,1,1,3-tetrachloropropane (HCC-250). HCC-240fa is an important intermediate in the preparation of 1,1,1,3,3-pentafluoropropane (HFC-245fa) an HFC blowing agent which is not destructive to the ozone layer.

2. Description of the Prior Art

The selective chlorination of partially halogenated alkanes is an important method for synthesizing halocarbon intermediates used in hydrofluorocarbon (HFC) production. Fluorine is subsequently introduced into the intermediate using hydrofluoric acid in the presence of a fluorination catalyst.

It is known in the art to photochlorinate alkanes. However, alkane photochlorinations are notoriously indiscriminate in regioselectivity. The presence of functional groups can have a rate disturbing effect and influence selectivity at nearby C—H sites in a manner that is often difficult to predict. Photochlorinations of alkanes bearing two or more C—H sites often result in poor selectivity. Because the Cl produced on photolysis is highly electrophilic, internal C—H bonds in simple alkanes are more reactive due to higher electron density than terminal C—H sites. Such photochlorination predominantly introduces chlorine atoms on the internal —CH$_2$— carbon atoms. The number and the location of nearby chlorine substituents modify the selectivity pattern, and the general outcome, and even the major product, cannot always be predicted with much certainty. For example, in the photochlorination of different chloroethanes, Migita, et al., in Bull. Chem. Soc. Japan, 1967, 40, 920, describe how successive introduction of chlorine at the 1-position decreases the reactivity of the 2-position, but in some cases it can increase the chlorination rate at the 1-position.

According to this invention it has been found that photochlorination of 1,1,1,3-tetrachloropropane efficiently introduces chlorine predominantly on the terminal —CH$_2$Cl group to produce 1,1,1,3,3-pentachloropropane as the major product. The only other feasible process for producing HFC-240fa involves adding carbon tetrachloride to vinyl chloride. Vinyl chloride is extremely toxic and its presence must be monitored closely through all phases of its use. The photolytic preparation of 1,1,1,3,3-pentachloropropane is advantageous by avoiding the use of vinyl chloride.

The most common methods for preparing specific 3-carbon polyhalocarbons involves adding a polyhalocarbon to an alkene. See, for example, U.S. Pat. No. 4,605,802. However, sluggish reactivity or telomerization to undesired high molecular weight products often accompany the desired adduct under normal conditions. These technologies require high pressure and temperature; glass lined pressure reactors; CuCl+amine activator as catalysts; typically 50% of volume as solvent such as acetonitrile; a more complicated recovery of solvent, catalysts, unreacted CCl$_4$ and vinyl chloride, and distillation product. In the herein described disclosure, important process advantages achieved include reaction at atmospheric pressure and ambient temperature; simple, glass lined reactors are used; no metal catalyst is employed; very high productivity/volume is attained since no solvent is present; and simple fractional distillation at reduced pressure to recover unreacted HCC-250 and purify the product.

SUMMARY OF THE INVENTION

The invention provides a process for the preparation of 1,1,1,3,3-pentachloropropane which comprises contacting 1,1,1,3-tetrachloropropane with chlorine in the presence of sufficient ultraviolet light and under conditions sufficient to thereby produce 1,1,1,3,3-pentachloropropane.

DETAILED DESCRIPTION OF THE PREFERRED EMBODIMENT

In the practice of the present invention 1,1,1,3,3-pentachloropropane is prepared by contacting 1,1,1,3-tetrachloropropane with sufficient chlorine in the presence of sufficient ultraviolet light under conditions sufficient to produce 1,1,1,3,3-pentachloropropane. The general reaction scheme is:

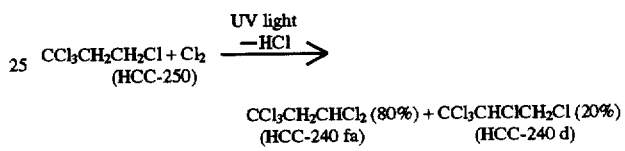

HCC-250 is well known in the art. It may be prepared according to the method described in U.S. Pat. No. 4,605,802 which is incorporated herein by reference. In general it may be prepared by the reaction of CCl$_4$ with ethylene catalyzed by a mixture of triethyl phosphite (TEP) and iron (O) powder in the absence of solvent. The process is conducted in a metal autoclave achieving 90+% conversion and 90+% selectivity at 95° C. and 110 psig in 12 hours. Ferric chloride is an optional co-catalyst to reduce the induction period that often accompanied this reaction. The production of HCC-250 under relatively mild operating conditions in glass reactors is readily achieved.

In the preferred embodiment, the reaction is conducted with less than the stoichiometric amount of elemental chlorine to replace one hydrogen atom on the 3-carbon of CCl$_3$CH$_2$CH$_2$Cl. In the preferred embodiment, the molar amount of molecular Cl$_2$ reacted per mole of HCC-250 ranges from about 25 mole % to about 99 mole %. A more preferred range is from about 25 mole % to about 80 mole % and most preferably from about 25 mole % to about 65 mole %. The chlorine is preferably in gaseous form and the HCC-250 in liquid form. The chlorine gas is contacted with the HCC-250 by bubbling chlorine gas into a bath of the HCC-250 liquid.

The reaction may be conducted at any convenient temperature and pressure, for example at temperatures of from about 0° C. to about 30° C. at standard atmospheric pressure. The temperatures and pressures are not critical, although temperatures of room temperature or slightly below are preferred. Temperature has only a modest effect on photochlorinations, however, higher temperature typically decrease selectivity.

These mild conditions permit glass reactors and glass peripheral equipment to be employed rather than using a high pressure apparatus. Neither solvents nor metal species are necessary, thus simplifying all aspects of the process. Preferably the reaction is conducted in the absence of oxygen and more preferably under a nitrogen blanket.

During chlorine contact with the HCC-250, the reaction mixture is exposed to UV radiation in an amount sufficient to cause a reaction of the reactants to produce HCC-240fa. UV irradiation is conducted using standard medium pressure mercury UV quartz immersion lamps. The reaction is typically conducted for from about 1 hour to about 20 hours, more preferably, from about 2 hours to about 10 hours and most preferably from about 2 hours to about 8 hours. The ultraviolet light preferably has a wavelength in the range of from about 265 nm to about 435 nm. In the preferred embodiment, ultraviolet light has a power in the range of from about 10 watts to about 500 watts, preferably from about 100 watts to about 450 watts. The amount and duration of exposure can be more or less than these quantities depending on conditions selected by the skilled artisan.

The desired HCC-240fa may be separated from reaction by-products and unreacted starting materials by known methods, such as fractional distillation by techniques well known in the art. The HCC-240 may be subsequently fluorinated using standard technology employing anhydrous hydrofluoric acid in the presence of a catalyst such as $SbCl_5$ to produce 1,1,1,3,3-pentafluoropropane (HFC-245fa).

Generally photochlorinations occur in a stepwise manner, with little dichlorination arising from an initial activated complex. In the monochlorination of HCC-250 all experiments show very similar selectivity profiles producing a virtually identical 4.2–4.5:1 ratio of HCC-240fa: HCC-240d throughout the entire course of reaction. This is the kinetic monochlorination product distribution controlled by the relative rate of electrophilic Cl• attack at $C_3$ vs. $C_2$. This is not a predictable ratio. A —$CCl_3$ group with its electron withdrawing inductive effect retards reactivity at an adjacent C—H bond. This latter effect predominates in the case of HCC-250 resulting in the preferred chlorination at $C_3$ to give pentachloropropane HCC-240f. As the conversion of the HCC-250 proceeds, sufficiently concentrated HCC-240 isomers undergo subsequent photochlorination to the HCC-230 isomers at a measurable rate. Increasing chlorine content in a hydrochlorocarbon increasingly deactivates it toward further photochlorination. Thus, high levels of the desired HCC-240f are generated before appreciable overchlorination occurs. It is significant to note that even where a high concentration of chlorine is pre-added to the reaction mixture the selectivity remained unchanged from that during slower feed of chlorine.

The following non-limiting examples serve to illustrate the invention.

EXAMPLE 1

Preparation of 1,1,1,3-Tetrachloropropane (HCC-250)

Carbon tetrachloride, 33.16 g (0.216 mol) and triethyl phosphite, 0.39 g (0.0023 mol) were added via syringe to a dried, evacuated 100 ml glass pressure reactor that already contains 0.152 g (0.0027 mol) of iron powder and 0.020 g (0.1 mmol) of $FeCl_3$, a magnetic stir bar, pressure gauge, and ball valve. The mixture was triply freeze-pump-thaw degassed (or the $CCl_4$ could be sparged with $N_2$ for 60 min. prior to the addition.) The stirred mixture was heated to 110° C. in a circulating constant temperature oil bath. After 15 minutes the reactor was briefly charged with ethylene gas to a pressure of 90 psig and then resealed. Over a period of 6 hours at 110° C. the reaction mixture was similarly charged with 5 additional pulses of ethylene. GC analysis revealed 50% conversion to $CCl_3CH_2CH_2Cl$, which was formed in >90% selectivity.

EXAMPLE 2

Photochlorination Procedure and Results

In this example, all photochlorinations were performed in a 0.8L jacketed glass reactor with a ¼" pfa gas inlet line for $N_2$ or chlorine, a teflon coated thermocouple, sampling port, reflux condenser (−15° C.) gas exit line connected to a 1L backflow trap, water scrubber, 20% aqueous KOH scrubber, dry ice trap and an oil bubbler leading directly into hood exhaust. The reactor is covered with aluminum foil. The UV light which situated in a quartz immersion well, is a 450 W (Runs 1 and 2 in Table 1), or 100 w (all other runs) medium pressure Hanovia Hg arc lamp. The pressure regulated chlorine feed, from a supported cylinder sitting on a balance, was controlled through a flowmeter, into a 1L backflow trap, through a ¼" pfa line inserted into the bottom of the magnetically stirred reaction mixture.

A 972.9 (5.35 mol) sample of 1,1,1,3-tetrachloropropane, commercially available at >99% (area) purity by GC analysis, was added to the photoreactor. This material, cooled to −10° C., was deoxygenated by slowly bubbling dry $N_2$ through the stirred liquid for 1 hour. Reagent grade $Cl_2$ supplied by Air Products and Chemicals, Inc. was continuously bubbled during photochlorination at a temperature ranging from about 5° C. to about 20° C. $Cl_2$ is highly soluble in 1,1,1,3-tetrachloropropane. Liquid samples of the product mixture were periodically withdrawn from the reactor during photochlorination and analyzed by gas chromatography and proton NMR spectroscopy. Reference samples of HCC-240 and HCC-230fa are used for verification. All other products were identified by gas chromatography/mass spectrometry, and comparison of their distinct NMR spectra with literature data. The results for this Example 2 are shown as Run 4 in Table 1.

Upon completing the photochlorination the product mixture, freed of any dissolved $Cl_2$ and hydrochloric acid, weighed 1049 g, representing 98.9% material balance at 46.1% conversion to a 95:5 mole ratio of HCC-240:HCC-230 isomers. The desired 1,1,1,3,3-pentachloropropane, boiling point 74° C. at 28 mm Hg (95% pure by GC area), is separated by fractional distillation from 1,1,1,2,3-pentachloropropane, boiling point 64° C. at 14 mm Hg (90% purity).

The estimated photochlorination production efficiency $E_{C12-UV}$ is defined as: $E_{C12-UV}$=M total moles $Cl_2$ pdts formed/hr/MTh. moles photons absorbed by the system/hr; where MTh. moles photons absorbed by the system/hr= Theoretical UV Photon Output/hr=Einsteins/hr=Σ(kjoules/hr)(λ in nm)/119620 for near uv λ output from 265 nm–435 nm=0.0515 g moles photons/hr for 100 W UV lamp=0.447 g moles photons/hr for 450 W UV lamp.

It is assumed that the theoretical spectral output is accurate and that photon absorption by $Cl_2$ is 100% efficient in this region of the spectrum. The efficiency for each product formed equals its mole fraction times the overall efficiency. The HCC-240fa efficiency results are shown in Table 2.

As shown by this Example, the photo-induced chlorination of HCC-250 introduces the additional chlorine predominantly on the $C_3$ terminal carbon, producing HCC-240fa with selectivity of 77% at a conversion of 46%. Furthermore, this selectivity is virtually unchanged at conversions of at least 50%. Selectivity for HCC-240fa remains near 70% even at 90% conversion. The major byproduct, the isomeric 1,1,1,2,3-pentachloropropane, is co-produced at a level of 18–20% selectivity. The remainder is comprised of overchlorination products HCC-230, HCC-220 and possibly traces of HCC-210. A production efficiency of 90% translates to a high quantum yield allowing significant HCC-240fa output for a given input of uv power.

EXAMPLE 3

Preparation of 1,1,1,3,3-Pentachloropropane (HCC-240fa)

930 g (5.1 mole) of HCC-250 is introduced into a 750 ml water-cooled reactor with quartz immersion well The HCC-250 was exposed to a 100 or 450 watt medium pressure Hanovia UV lamp while slowly and constantly feeding chlorine at a rate of 22 g (0.3 mole)/hr. The reaction is conducted at 5° C. At 16 hours and 82% conversion, GC/ms of the crude product mixture revealed two isomers of HCC-240 and two isomers of HCC-230. High resolution proton NMR confirmed this analysis and indicated an additional component, an isomer of HCC-230 or HCC-220, was also present. The product analysis at the end of 19 hours is shown as run 1 in Table 1 below. Analogous runs 2 and 3 are conducted under the conditions and with the results also indicated in Table 1.

TABLE 1

PHOTOCHLORINATION OF HCC-250

| Run # | UV lamp | hours | % Conv. | mol % of HCC | | | | |
|---|---|---|---|---|---|---|---|---|
| | | | | 240fa | 240d | 230fa | 230d | 220 |
| 1 | 450 w | 19 | 92 | 69 | 16 | 6 | 4 | 5 |
| 2 | 450 w | 7 | 71 | 75 | 18 | 3 | 2 | 2 |
| 3 | 100 w | 8 | 88 | 72 | 16 | 5 | 3 | 4 |
| 4 | 100 w | 1.25 | 46 | 77 | 18 | 1 | 1 | 2 |

TABLE 2

| Photochlorination | UV lamp | Hours | % Total Conv | Efficiency |
|---|---|---|---|---|
| #1 | 450 w | 19 | 92 | 0.6 |
| #2 | 450 w | 7 | 71 | 1.3 |
| #3 | 100 w | 8 | 88 | 11.5 |
| #4a | 100 w | 1 | 26.2 | 27 |
| #4b | 100 w | +5.5min. | 32.9 | 76* |
| #4c | 100 w | +6.0min. | 41.7 | 91 |
| #4d | 100 w | +3.0min. | 46.1 | 91 |

* = per time increment

What is claimed is:

1. A process for the preparation of 1,1,1,3,3-pentachloropropane which comprises contacting 1,1,1,3-tetrachloropropane with chlorine and in contact with sufficient ultraviolet light and under conditions to produce 1,1,1,3,3-pentachloropropane.

2. The process of claim 1 wherein the contacting is conducted with chlorine gas.

3. The process of claim 1 wherein the contacting is conducted with liquid 1,1,1,3-tetrachloropropane.

4. The process of claim 1 wherein chlorine gas is contacted with liquid 1,1,1,3-tetrachloropropane.

5. The process of claim 1 wherein the contacting is conducted with less than the stoichiometric amount of elemental chlorine per hydrogen atom on the 3 -carbon of $CCl_3CH_2CH_2Cl$.

6. The process of claim 1 which is conducted in the absence of oxygen.

7. The process of claim 1 which is conducted under a nitrogen atmosphere.

8. The process of claim 1 which is conducted at a temperature of from about 0° C. to about 30° C.

9. The process of claim 1 which is conducted at atmospheric pressure.

10. The process of claim 1 further comprising the subsequent step of separating 1,1,1,3,3-pentachloropropane from any reaction by-products and unreacted 1,1,1,3-tetrachloropropane.

11. The process of claim 1 further comprising the subsequent step of separating 1,1,1,3,3-pentachloropropane from any reaction by-products and unreacted 1,1,1,3-tetrachloropropane by distillation.

12. The process of claim 1 wherein the contacting is with a molar amount of molecular $Cl_2$ reacted per mole of 1,1,1,3-tetrachloropropane which ranges from about 25 mole % to about 99 mole %.

13. The process of claim 1 wherein the contacting is with a molar amount of molecular $Cl_2$ reacted per mole of 1,1,1,3-tetrachloropropane which ranges from about 25 mole % to about 80 mole %.

14. The process of claim 1 wherein the contacting is with a molar amount of molecular $Cl_2$ reacted per mole of 1,1,1,3-tetrachloropropane which ranges from about 25 mole % to about 65 mole %.

15. The process of claim 1 wherein the contacting is conducted for from about 1 hour to about 20 hours.

16. The process of claim 1 wherein the contacting is conducted for from about 2 hour to about 10 hours.

17. The process of claim 1 wherein the contacting is conducted for from about 2 hour to about 8 hours.

18. The process of claim 1 wherein the contacting is conducted with the ultraviolet light having a wavelength in the range of from about 265 nm to about 435 nm.

19. The process of claim 1 wherein the contacting is conducted with the ultraviolet light having a power in the range of from about 10 watts to about 500 watts.

20. The process of claim 1 wherein the contacting is conducted with the ultraviolet light having a power in the range of from about 100 watts to about 450 watts.

* * * * *